United States Patent [19]

Sheth et al.

[11] 4,167,558

[45] Sep. 11, 1979

[54] NOVEL SUSTAINED RELEASE TABLET FORMULATIONS

[75] Inventors: Prabhakar R. Sheth, Pearl River, N.Y.; Jacques L. Tossounian, Pine Brook, N.J.

[73] Assignee: Hoffmann-La Roche Inc., Nutley, N.J.

[21] Appl. No.: 957,948

[22] Filed: Nov. 6, 1978

Related U.S. Application Data

[60] Division of Ser. No. 872,181, Jan. 25, 1978, Pat. No. 4,140,755, which is a continuation of Ser. No. 658,003, Feb. 13, 1976, abandoned, which is a continuation-in-part of Ser. No. 559,107, Mar. 17, 1975, abandoned.

[51] Int. Cl.² .................. A61K 9/22; A61K 9/26; A61K 31/60
[52] U.S. Cl. .................. 424/22; 424/19; 424/35; 424/230; 424/362
[58] Field of Search .................. 424/19–22, 424/35, 362, 230

[56] References Cited

U.S. PATENT DOCUMENTS

| | | | |
|---|---|---|---|
| 3,065,143 | 11/1962 | Christenson et al. | 424/22 |
| 3,119,733 | 1/1964 | Nichols | 424/362 X |
| 3,418,999 | 12/1968 | Davis | 424/14 X |
| 3,427,378 | 2/1969 | Henderson et al. | 424/14 |
| 3,444,290 | 5/1969 | Wal | 424/4 |
| 3,449,489 | 6/1969 | Gaunt | 424/31 |
| 3,555,151 | 1/1971 | Kaplan et al. | 424/156 |
| 3,574,820 | 4/1971 | Johnson et al. | 424/22 |
| 3,976,764 | 8/1976 | Watanabe et al. | 424/19 |
| 4,126,672 | 11/1978 | Sheth et al. | 424/22 |
| 4,140,755 | 2/1979 | Sheth et al. | 424/21 |

FOREIGN PATENT DOCUMENTS

| | | |
|---|---|---|
| 623704 | 4/1963 | Belgium . |
| 1492132 | 9/1969 | Fed. Rep. of Germany . |
| 1467786 | 5/1972 | Fed. Rep. of Germany . |
| 2307747 | 8/1973 | Fed. Rep. of Germany . |
| 2357389 | 5/1974 | Fed. Rep. of Germany . |
| 1357737 | 6/1974 | United Kingdom . |

*Primary Examiner*—Shep K. Rose
*Attorney, Agent, or Firm*—Jon S. Saxe; George M. Gould; R. Hain Swope

[57] ABSTRACT

A novel sustained release formulation for the preparation of tablets for oral administration is disclosed. The formulation is hydrodynamically balanced to be buoyant in gastric juice thereby remaining in the stomach for an extended period of time.

2 Claims, No Drawings

NOVEL SUSTAINED RELEASE TABLET FORMULATIONS

CROSS-REFERENCE TO RELATED APPLICATIONS

This is a divisional application of application Ser. No. 872,181 filed Jan. 25, 1978, now U.S. Pat. No. 4,140,755 which in turn is a continuation of U.S. patent application Ser. No. 658,003, filed Feb. 13, 1976, now abandoned, which in turn is a continuation-in-part of U.S. patent application Ser. No. 559,107, filed Mar. 17, 1975, now abandoned.

BACKGROUND OF THE INVENTION

The convenience of administering a single dose of medication which releases active ingredient over an extended period of time as opposed to the administration of a number of single doses at regular intervals has long been recognized in the pharmaceutical art. The advantage to the patient and clinician in having consistent and uniform blood levels of medication over an extended period of time are likewise recognized. In most sustained release preparations known to the pharmaceutical art, medicinal agents are either coated with varying thicknesses of some type of relatively insoluble material or are imbedded into a rigid lattice of resinous material. In such preparations, the object is to continuously provide drug for absorption into the blood stream to replace the amount eliminated while the dosage form is passing through the gastrointestinal tract of the patient.

The conventional approaches to sustained release formulation briefly outlined above can be disadvantageous in that certain classes of active ingredients are not suited to absorption during passage through the gastrointestinal tract due to their physiochemical properties and/or favorable sites of absorption. For example, most acidic medicaments are principally absorbed from the stomach, whereas most basic medicaments are absorbed primarily from the intestines. Most medicaments will undergo varying degrees of change in solubility by passage from the acutely acidic conditions of the stomach to the neutral to alkaline conditions of the intestines. For example, ferrous salts are more soluble in the stomach than in the intestines. Finally, there are medicaments, e.g., antacids, which are intended to act in the stomach and therefore lose most beneficial properties when they pass into the intestines.

It is readily apparent in view of the above considerations that a large number of medicaments are not amenable to conventional sustained release formulations which are not retained in the stomach and which release medicament in the intestines. It is equally apparent that a sustained release formulation which is retained in the stomach and which slowly releases medicament in the stomach over an extended period of time would be eminently suited to such medicaments. Such a sustained release formulation is provided by the present invention.

The principle of sustained release which characterizes the tablets of the subject invention is unique in the art, i.e., the tablets remain buoyant and free floating in the gastric fluid for an extended period of time, during which substantially all of the medicament is released therefrom. Although many mechanisms of sustained release are recognized in the art and the concept of a floating tablet is recognized, there is no teaching which recognizes the application of buoyancy to sustained release as is taught by the subject invention.

For example, Davis U.S. Pat. No. 3,418,999 teaches a tablet which is buoyant. However, the buoyancy of the tablet is disclosed as being merely an adjunct to swallowing and there is no suggestion therein of applying the buoyancy to sustained release. The Davis tablets also must have an initial density of less than 1, whereas the tablets of the subject invention are not so restricted.

The concept of a table which swells when in contact with gastric fluid is also recognized in the art. For example, Johnson et al. U.S. Pat. No. 3,574,820 teach tablets which swell in contact with gastric fluids to a size such that they cannot pass the pylorus and therefore are retained in the stomach. It is readily apparent that such tablets are not buoyant since, if they were, their size in relation to being able to pass the pylorus would be of no consequence.

The incorporation of a swellable hydrocolloid in a sustained release tablet is also recognized in the art. Playfair U.S. Pat. No. 3,147,187 teaches incorporation of a swelling gum or proteinaceous material into a sustained release tablet to aid in disintegration of the tablet and thus expose more surface to digestion. There is no indication that the disclosed tablets are intended to be buoyant. This is further evidenced by the fact that all ingredients are combined into a melt which is thereafter cooled and granulated. The hydrocolloid is therefore formulated in the manner of a conventional tabletting binder as opposed to being added to the formulation in a dry particulate form as in the practice of the subject invention whereby it functions to facilitate the buoyancy of the tablet.

Finally, Christenson et al. U.S. Pat. No. 3,065,143 teach the use of a hydrocolloid in a sustained release tablet to form a water impermeable barrier on the outer surface of the tablet which gradually erodes and thus releases medicament over an extended period of time. There is no suggestion, however, that such phenomenon could be utilized to achieve a hydrodynamic balance for a tablet such that it will remain floating on the gastric fluid in the stomach for an extended period of time as in the subject invention.

BRIEF DESCRIPTION OF THE INVENTION

Formulations suitable for the preparation of sustained release tablets for oral administration are provided. The formulations comprise one or more medicaments in combination with a hydrocolloid so as to be hydrodynamically balanced so that, in contact with gastric fluid, they have a bulk density (specific gravity) less than one and therefore are buoyant in gastric fluid and thus are retained in the stomach during the time when substantially all of the medicaments are released therefrom.

DETAILED DESCRIPTION OF THE INVENTION

In accordance with the present invention, formulations for the preparation of sustained release tablets for oral administration are provided which are hydrodynamically balanced to have a bulk density (specific gravity) of less than one in contact with gastric fluid and which, therefore, will remain floating in gastric fluid which has a specific gravity of between 1.004 and 1.010. The sustained release formulations of the present invention comprise a homogeneous mixture of one or more medicaments with one or more hydrophillic hydrocolloids which, in contact with gastric fluid at body temperature, will form a soft gelatinous mass on the surface of the tablet, thus causing it to enlarge somewhat and acquire a bulk density (specific gravity) of less than one. The medicament is slowly released from the surface of the gelatinous mass which, due to its buoyancy, remains buoyant in the gastric fluid. Ultimately, after substantially all of the medicaments therein are released, the gelatinous mass disperses.

Upon oral ingestion of sustained release tablets prepared from the tablet film coating, if such is present, dissolves leaving the contents in contact with gastric fluid. Upon contact with gastric fluid, the outermost hydrophillic colloid particles hydrate to form an outside barrier which enlarges the tablet somewhat while substantially retaining the shape thereof and therefore acts to prevent the mass from disintegrating. The hydrated outer layer thereafter slowly dissolves releasing medicament. There is also a release of medicament by leaching action at or near the surface of the mass. As new surface is exposed to gastric fluid it, in turn, becomes hydrated, thus maintaining the integrity of the barrier. This process is continuously repeated until the medicament is substantially leached out. Thereafter, the remaining matrix which is still buoyant in gastric fluid slowly dissolves and is eliminated. It has been found that the release pattern and resulting blood levels attained with the sustained release formulation of the invention has advantages over other sustained release mechanisms known in the art, particularly wherein the medicament contained therein is principally absorbed and/or exerts its therapeutic activity in the stomach or duodenum. Sustained release tablets prepared in accordance with the present invention unexpectedly produce optimum blood levels with certain medicaments, e.g., chlordiazepoxide. The results with chlordiazepoxide were superior to known sustained release formulations previously tried, each of which had failed to produce satisfactory blood levels. In addition, the sustained release formulation of the present invention unexpectedly provides an excellent means for administering antacid substances over a prolonged period of time.

Hydrocolloids suitable for use in the sustained release formulations of the subject invention include one or more natural, partially or totally synthetic anionic or, preferably, nonionic hydrophillic gums, modified cellulosic substances or proteinaceous substances such as, for example, acacia, gum tragacanth, locust bean gum, guar gum, karaya gum, agar, pectin, carrageen, soluble and insoluble alginates, methylcellulose, hydroxypropylmethylcellulose, hydroxypropylcellulose, hydroxyethylcellulose, sodiumcarboxymethylcellulose, carboxypolymethylene (Carbopol-Cabot Corporation), gelatin, casein, zein, bentonie, Veegum (R. T. Vanderbilt Co.) and the like. A preferred hydrocolloid in accordance with the present invention is hydroxypropylmethylcellulose. The use of such materials in pharmaceutical compounding is recognized in the art. For example, Kaplan et al. U.S. Pat. No. 3,555,151 discloses the use of such hydrocolloids in sustained release antacid preparations.

In order to successfully practice the present invention, the hydrocolloids utilized must hydrate in acidic medium, i.e., gastric fluid with a pH equivalent to 0.1 N hydrochloric acid, i.e., a pH of approximately 1.2. Furthermore, although the initial bulk density of the tablets of the invention may initially be greater than one, it is essential that the formulation be hydrodynamically balanced to have a bulk density of less than one when in contact with gastric fluids to assure buoyancy. There are a number of methods whereby the rate of release of medication from the sustained release tablets of the present invention can be adjusted. First, the choice of a particular hydrocolloid or mixture of hydrocolloids can affect the release rate, e.g., high viscosity hydrocolloids, e.g., methylcellulose 60 HG, 4000 cps, hydrate more slowly and maintain a soft mass for a longer time than low viscosity hydrocolloids, e.g., methylcellulose 60 HG, 10 cps. Further, edible, pharmaceutically inert, fatty materials having a specific gravity of less than one can be added to the formulation to decrease the hydrophillic property of the formulation and also to increase buoyancy. Examples of such materials include: a purified grade of beeswax; fatty acids; long chain fatty alcohols such as, for example, cetyl alcohol, myristyl alcohol, stearyl alcohol, glycerides such as glyceryl esters of fatty acids or hydrogenated aliphatic acids such as, for example, glyceryl monostearate, glyceryl distearate, glyceryl esters of hydrogenated castor oil and the like; oils such as mineral oil and the like.

There may also be incorporated into the sustained release tablets of the present invention additional edible non-toxic ingredients recognized in the art of pharmaceutical compounding such as excipients, preservatives, stabilizers, tabletting lubricants and the like. The choice of such materials and the amounts to be utilized are considered to be within the purview of one skilled in the art. It is to be borne in mind, however, that such conventional pharmaceutical adjuncts which might adversely affect the hydrodynamic balance of the sustained release formulation of the present invention are not suitable for use therein.

The amount of the active medicament or mixtures thereof in the sustained release tablet of the present invention can vary over a wide range, i.e., from about 0.1% by weight to about 90% by weight. The amount of active substances present is usually between about 5% by weight and 50% by weight. Factors which govern the amount of active substance present in the sustained release tablets of the present invention are, for example, the amount required to give full therapeutic dosage, the bulk density thereof, the hydrophillic or hydrophobic properties thereof, the stability thereof and the like. These properties are known or are easily ascertainable by a person skilled in the art and the formulation adjustments required to incorporate any given therapeutically active substance into a sustained release tablet in accordance with the present invention are considered to be within the purview of the art. The amount of the hydrocolloid ingredient present in the sustained release tablet of the present invention may also vary within a wide range, i.e., from about 5% by weight to about 99.9% by weight. Again, the amount of hydrocolloid ingredient to be utilized will vary in relation to the amounts and properties of the active ingredient and inert pharmaceutical adjuncts utilized. Generally, the amount of hydrocolloid present will be between about 20% by weight and about 75% by weight.

Wherein one or a mixture of fatty materials is present in the sustained release tablets of the invention, such material comprises up to about 60% by weight of the total formulation. In general, wherein the formulations do contain a fatty material, such material is present in from about 5% by weight to about 30% by weight. The amount of fatty material utilized is governed by the amounts and physical characteristics of both the active ingredient and the hydrocolloid with the object being to achieve a hydrodynamically balanced formulation, i.e., a formulation which acquires a bulk density (specific gravity) of less than one in gastric fluids.

The amount of edible, inert pharmaceutical adjunct materials which may be present in the sustained release tablets of the present invention will also vary in accordance with the amounts and physical properties of the other ingredients. Such materials having a bulk density less than 1, e.g., ethylcellalose. More importantly, it is possible to utilize the selection of inert pharmaceutical adjunct materials to modify the rate of release of the formulation. For example, soluble excipients, e.g., lactose, mannitol and the like, will increase the rate of release whereas insoluble excipients, e.g., dicalcium phosphate, terra alba and the like, will decrease solubility. Wherein such pharmaceutical adjunct materials are included in the formulations of the invention, they can be present in up to 80% by weight of the final formulation. Generally, such conventional pharmaceutical adjuncts are present in from about 5% by weight to about 60% by weight of the formulation. The inclusion of and choice of such materials is again considered to be within the purview of the art utilizing the principles of the present invention.

The hydrodynamically balanced sustained release dosage tablets of the present invention are prepared for compression into tablets by techniques well established in the art. In most instances it is necessary to utilize the technique of wet granulation followed by compression into tablets. However, where the physical properties of the ingredients will permit, tablets may be prepared by direct compression of a homogeneous mixture of the ingredients. Such tablets contain conventional tabletting lubricants and may also contain other pharmaceutical adjunct materials in accordance with the criteria set forth herein. It is to be noted that many of the hydrocolloids utilized in the practice of the invention are conventionally used in pharmaceutical compounding as tablet binders and as such, are incorporated into the tablet formulation in the form of a solution or dispersion in a suitable solvent. In the practice of the invention, however, the hydrocolloid ingredient is incorporated into the formulation in "dry" form, i.e. excluding it from wet granulation techniques where they are utilized. However, a small percentage of the hydrocolloid ingredient may be utilized in accordance with convention techniques as a tablet binder. Wherein a hydrocolloid such as described herein is utilized conventionally as a tablet binder and is combined into the formulation in the presence of a solvent, such hydrocolloid does not function to facilitate the buoyancy of the tablets prepared therefrom.

Tablets prepared in accordance with the present invention can be manufactured on conventional tabletting equipment. However, it is critical that they are not compressed to a degree of hardness such that they will not acquire a bulk density of less than one in contact with gastric fluids. In accordance with the present invention, tablets which initially have a density greater than one will be buoyant in gastric fluids. This buoyancy results from a combination of an increase in the bulk volume of the tablet when it contacts gastric fluids due to the hydration and swelling of the hydrocolloid particles on the tablet surface and the internal voids in the tablet center remaining dry due to the barrier formed by the hydrocolloid particles. Therefore, it is critical that the tablets are not compressed to a degree of hardness such that the porosity is materially reduced and the hydrocolloid particles on the tablet surface are compacted so tightly that rapid hydration is retarded. It will be appreciated that the maximum hardness to which a tablet having an initial density greater than one can be compressed will vary both with the initial density of the formulation and the size of the tablet. The hardness for any tablet will lie between the maximum at which a buoyant tablet can be produced in accordance with the teachings herein and a minimum required for tablets to meet basic pharmaceutical tests of stability during shipment, and the like. This range of hardness can be easily determined by standard pharmaceutical hardness measurements combined with testing of the buoyancy of samples of tablets different hardness in gastric fluid. Such determinations are considered to be within the skill of the skilled artisan.

The medicament or combination of medicaments which are amenable to sustained release therapy utilizing the novel formulations of the present invention include any of those suitable for oral administration where sustained release therapy is medically advisable. It is to be understood that the present invention is not to be construed as being limited to any particular medicament or class of medicaments. Further, the sustained release tablet of the present invention is not restricted to medicaments which are principally absorbed from the stomach since it has been found that it is equally efficacious with medicaments which are absorbed from the intestines, e.g., chlorpheniramine maleate. The sustained release dosage formulation of the invention could obviously not be utilized with medicaments which are acid sensitive. Among the various classes of medicaments which are advantageously administered via a sustained release dosage form are, for example, antibiotics, e.g., penicillins, cephalosporins and tetracyclines; catecholamines, e.g., epinephrine and the amphetamines; analgesics, e.g., aspirin; sedatives, e.g., the barbiturates, anticonvulsants, antinauseants, muscle relaxants, hypotensives, the vitamins and the like. It is reported in the literature that the irritation of the stomach caused by aspirin is the result of contact of this very acidic substance with the stomach walls. Therefore, it will be appreciated that the formulations of the invention are particularly advantageous for the administration of aspirin since they remain buoyant in gastric fluid.

A class of medicaments to which the sustained release tablet of the subject invention is particularly amenable is the benzodiazepines, e.g., chlordiazepoxide, diazepam, oxazepam, bromazepam and the like. It is noteworthy that, after a number of sustained release mechanisms known to the art proved unsuccessful, superior results were obtained with chlordiazepoxide utilizing for formulations of the subject invention.

The sustained release tablets of the present invention are also particularly amenable to the administration of medicaments which are only absorbed through the stomach or upper portion of the intestines, e.g., ferrous salts such as ferrous fumarate, or which exert a therapeutic effect in the stomach, for example, antacids such as the oxides, hydroxides and carbonates of magnesium, aluminum hydroxide, magnesium trisilicate and the like. Wherein such substances generate carbon dioxide, bubbles will become entrapped by the hydrated outer layer thus enhancing the buoyancy of the tablet. Small amounts of carbon dioxide generating bases can also be utilized in non-antacid formulations to enhance buoyancy. It is further within the scope of the present invention to administer the formulations hydrodynamically balanced in accordance with the invention as one layer of a two layer tablet. The remaining layer contains medicament in a conventional formulation free of sustained release ingredients. This unique tablet, upon ingestion, provides an immediate release of medicament and a buoyant layer which continues to release medicament over a period of time while being retained in the stomach. Such unique two-layered tablets are particularly advantageous for the administration of antacid substances.

The sustained release tablet of the present invention has been found to remain buoyant in gastric fluid despite the presence of surfactants or food. The efficacy of medicaments administered utilizing the sustained release formulation of the present invention has been found to be independent of the site of absorption of the particular medicament. Utilizing dogs which had ingested capsules containing barium sulfate in the formulation in accordance with the present invention, it has been demonstrated by the use of x-ray techniques that the formulation remains buoyant in the gastric fluid and does not adhere to the walls of the stomach.

The following examples further illustrate the invention.

EXAMPLE 1

Riboflavin tablets were prepared from the following formulation:

| Ingredient | mg/tablet |
| --- | --- |
| Riboflavin-5'-Phosphate Sodium* | 21.4 |
| Methylcellulose  4000 cps | 70.0 |
| Mannitol | 25.0 |
| Sodium carboxymethylcellulose, high viscosity, degree of substitution 0.38-0.48 | 110.0 |
| Hydroxypropylmethylcellulose 4000 cps | 60.0 |
| Polyvinylpyrrolidone | 20.0 |
| Ethylcellulose 10 cps | 80.6 |
| Talc | 10.0 |
| Magnesium Stearate | 3.0 |
| Total | 400.0 |

*Contains 2% by weight excess.

The riboflavin and sodium carboxymethylcellulose were thoroughly mixed and granulated with the polyvinylpyrrolidone as a 10% by weight solution in alcohol. The remaining ingredients with the exception of the talc and magnesium stearate were thoroughly mixed and passed through a Fitzpatrick Comminuting Machine using a #1 screen, hammers forward. The granulation was combined with this mixture and thoroughly mixed. The talc and magnesium stearate were then added and the total mixture homogeneously blended and compressed into tablets using standard concave punches. The tablets were compressed to a hardness of 4-6 s.c.u. and it was determined that the hardness should not exceed 10 s.c.u. It was found that tablets at 4 s.c.u. would float instantly on artificial gastric fluid, whereas tablets at 6 s.c.u. would sink temporarily before rising to the surface. Tablets at 10 s.c.u. were not buoyant.

For control purposes, gelatin capsules were filled with the following formulation:

| Ingredient | mg/capsule |
| --- | --- |
| Riboflavin-5'-Phosphate Sodium | 21.4 |
| Cornstarch | 73.6 |
| Lactose, hydrous | 150.0 |

-continued

| Ingredient | mg/capsule |
| --- | --- |
| Talc | 30.0 |
| Magnesium Stearate | 5.0 |
| Total | 280.0 |

In vitro release tests were carried out by the modified N.F. method in gastric fluid only at 40 r.p.m. The results are set forth in the following table:

TABLE

| Time (Hours) | Average | Percent Active Ingredient Released Range |
| --- | --- | --- |
| ½ | 32 | 27-40 |
| 1 | 49 | 39-59 |
| 2 | 76 | 55-87 |
| 3½ | 91 | 87-95 |
| 5 | 104 | 95-108 |

One-hundred percent of the riboflavin contained in the control capsule was released within one-half hour.

An in vivo test was conducted utilizing five volunteers. The dosage forms were administered about 1½ hours after breakfast. Periodic urine samples were analyzed for recovery of riboflavin which is an index of absorption. The results are given in the following table:

TABLE

| Time Interval (Hours) | Mg. of riboflavin excreted due to dose (Mean) | |
| --- | --- | --- |
| | Control | SR Tablet |
| 0-2 | 2.03 | 0.98 |
| 2-4 | 2.11 | 1.79 |
| 4-6 | 0.84 | 1.14 |
| 6-8 | 0.47 | 1.14 |
| 8-12 | 0.84 | 3.23 |
| 12-24 | 0.38 | 1.86 |
| | 6.87 | 10.14 |
| Percent of Dose Excreted in 24 hours | 44% | 67.5% |

The results of this experiment clearly indicate that the SR tablet containing riboflavin was retained in the stomach since the absorption of riboflavin occurs only from the proximal end of the small intestine. The results clearly indicate that riboflavin is continuously available from the SR tablet to the appropriate site of absorption for a prolonged period. The second pronounced peak of riboflavin from the tablet might be due to enterohepatic circulation which, according to the literature, may be attributable to a concentration dependent relationship in handling of riboflavin by the liver.

EXAMPLE 2

Sustained release aspirin tablets containing 7.5 grains aspirin were prepared from the following granulations:

| Granulation A | Mg. |
| --- | --- |
| Acetylsalicyclic Acid | 500 |
| Hydroxypropylmethylcellulose, 400 cps | 125 |
| Hydroxypropylmethylcellulose, 15 cps | 3 |
| Total | 628 |
| Granulation | |
| Calcium Carbonate, precipitated | 65 |
| Magnesium Carbonate | 20 |
| Mannitol | 10 |
| Carboxymethylcellulose | 2 |
| Total | 97 |

The two granulations were homogeneously mixed with 5 mg. talc and compressed using capsule-shaped punches to a hardness of 5 to 6 S.C.U. Hardness should not exceed 11 S.C.U. for tablet to remain buoyant.

EXAMPLE 3

Sustained release two-layered antacid tablets were prepared as follows:

| Layer A-Immediate Release Ingredient | mg/tablet |
|---|---|
| FMA-11* | 160.0 |
| Methylcellulose | 5.8 |
| Magnesium Oxide | 80.0 |
| Primojel** | 10.0 |
| Magnesium Stearate | 2.5 |
| Total | 258.3 |

*Aluminum hydroxide-magnesium carbonate co-precipitate - Reheis Co.
**Sodium carboxymethyl starch - E. Mendel & Co., Carmel, New York The FMA-11 and magnesium oxide were mixed in a suitable mixer. The resulting mixture was granulated utilizing a 2.5% by weight solution of the methylcellulose in a mixture of equal parts water and ethyl alcohol. The granulation was dried overnight at 60° C. The dried granulation was then milled, combined with the Primojel and magnesium stearate and mixed for five minutes. The resulting homogeneous mixture was then compressed on a conventional two-layer tablet press.

| Layer B-Sustained Release Ingredient | mg/tablet |
|---|---|
| FMA-11 | 170 |
| Magnesium Oxide | 85 |
| Methylcellulose 4000 cps (dry) | 90 |
| Methylcellulose 4000 cps (wet) | 6 |
| Ethylcellulose | 90 |
| Direct Compression Grade Starch | 35 |
| Syloid* | 30 |
| Magnesium Stearate | 23 |
| Total | 529 |

*Purified silicon dioxide - W. R. Grace & Co., Baltimore, Maryland

The FMS-11 and the magnesium oxide were mixed in a suitable mixer. The resulting mixture was granulated with a solution of the methylcellulose (wet) in a mixture of equal parts water and ethyl alcohol and the granulation dried overnight at 60° C. The resulting granulation was combined with the methylcellulose (dry), ethylcellulose, direct compression grade starch and Syloid and thoroughly mixed for about 10 minutes. The magnesium stearate was added and the mixture mixed for an additional five minutes. This mixture was then compressed on a conventional two-layer tabletting machine with Layer A to a standard concave capsule shape ¾"×5/16". The acceptable hardness of the tablets was between 12 and 14 s.c.u. and it was found that the hardness could not exceed 16 s.c.u.

A sample of the two-layer antacid tablets thus formed was placed in a beaker containing gastric fluid and equipped with a magnetic stirrer running at slow speed. It was observed that the immediate release layer separated and sank to the bottom of the beaker in fine particulate form. The sustained release layer remained floating for two hours slowly releasing medication.

We claim:

1. A sustained release pharmaceutical tablet containing as the active ingredient acetylsalicylic acid, said tablet being hydrodynamically balanced so that, upon contact with gastric fluid, said tablet acquires and maintains a bulk density of less than one thereby being buoyant in said fluid and remaining buoyant in the gastric fluid of the stomach until substantially all of the acetylsalicylic acid contained therein has been released therefrom, said tablet comprising a homogeneous mixture of acetylsalicylic acid, from about 0% to about 80% by weight of therapeutically inert, pharmaceutically acceptable adjunct materials, and from about 20% by weight to about 75% by weight of one or a mixture of hydrocolloids selected from the group consisting of methyl cellulose, hydroxypropylcellulose, hydroxypropylmethylcellulose, hydroxyethylcellulose and sodium carboxymethylcellulose to provide, upon contact with gastric fluid, a water impermeable barrier on the surface of said tablet, said tablet being compressed to a hardness of from about 5 to about 6 S.C.U.

2. The sustained release tablet in accordance with claim 1 wherein said hydrocolloid is hydroxypropylmethylcellulose.

* * * * *